United States Patent [19]

Mikkelsen

[11] Patent Number: Plant 5,953

[45] Date of Patent: Apr. 21, 1987

[54] BEGONIA PLANT NAMED ROMANCE TOO

[75] Inventor: James C. Mikkelsen, Ashtabula, Ohio

[73] Assignee: Mikkelsens, Inc., Ohio

[21] Appl. No.: 554,707

[22] Filed: Nov. 23, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of begonia plant known by the name Romance Too characterized by its light chartreuse-yellow flower color, which fades to a lighter yellow on maturity, with the outermost petals turning to pink on maturity; ease of propagation; vigorous growth habit; early flowering, and excellent keeping quality.

1 Drawing Figure

The present invention relates to a new and distinctive cultivar of begonia plant, botanically known as hiemalis begonia, Fotsch, and known by the cultivar name Romance Too.

The new cultivar was discovered by me as a mutation of the unpatented cultivar Romance. Romance Too was observed in a group of plants derived from tissue cultured irradiated plant material of the parent cultivar.

Asexual reproduction by stem and/or leaf cuttings by me at Ashtabula, Ohio has reproduced the unique features of the new cultivar through successive propagations.

The following characteristics distinguish the new begonia from both its parent and other begonias commercially known and used in the floriculture industry:

1. The unique light chartreuse-yellow color of the flowers, the color being a darker shade than the parent cultivar Romance.

2. In comparison to Romance, the new cultivar propagates more readily, producing 30% more adventitious shoots consistently in all seasons.

3. The new cultivar is a more vigorous grower than the parent.

4. Romance Too is more floriferous and the flower size is larger than in Romance.

5. The tepals are less susceptible to botrytis petal blight than the tepals of the parent.

6. The keeping quality of the flowers is superior in the winter months in Ohio when bud drop is a problem in many commercial begonia cultivars.

7. Romance Too is considered an early flowering cultivar, blooming in 7 to 8 weeks in summer to 10 weeks in winter when flowering can be controlled by short day treatment.

8. Readily propagated by leaf cuttings and stem cuttings, the latter technique being idealy suited for quick turnover crops in 9–10 cm. pots.

The accompanying colored photograph taken in November 1983 illustrates in perspective view the overall appearance of Romance Too, showing the colors as true as it is reasonably possible to obtain in a colored reproduction of this type.

The following is a detailed description of my new begonia cultivar based on plants produced under commercial practices in the greenhouses of Mikkelsens Inc., Ashtabula, Ohio in 10 cm. plastic pots using a multi-shooted leaf cutting. Color references are made to The Royal Horticultural Society Colour Chart except where general color terms of ordinary dictionary significance are used. It should be noted that temperature, light levels, and nutrition greatly affect the color of the flowers and foliage on begonia cultivars of this type.

Parentage: A pink Mikkelsen begonia seedling (never commercialized) was irradiated with gamma rays at Michigan State University in 1977 and gave rise to the cream colored cultivar Romance. The cultivar Romance was irradiated with gamma rays at Penn State University in the autumn of 1981, then tissue culture propagated. The new cultivar Romance Too was selected in the summer of 1982. Continuous testing indicates that the new selection is stable and reproducable.

Propagation:

(A) *Type cutting.*—Leaf cutting with 5–7 mm. petiole.

(B) *Time to visible roots.*—12–14 days at 75° C. summer, 15–20 days at 75° C. winter.

(C) *Rooting habit.*—Fibrous, dendritic, abundant.

(D) *Time for shoot development.*—Shoots 4 cm. long develop in 7–8 weeks in summer to 10–12 weeks in winter.

Plant description:

(A) *Form.*—Low, generally very compact, close internodes, bush type plant; herbaceous; produces pseudotuberous root growth during short days and low temperatures.

(B) *Habit of growth.*—Sturdy, medium growth, at times extremely self-branching. This feature, combined with above average adventitious shoot count, produces a well rounded uniform looking plant with delayed flowering when large numbers of shoots are present.

(C) *Foliage.*—Simple, alternate, borne on strong rigid petioles; average quantity for hiemalis begonias; there appears to be more resistance to powdery mildew than most hiemalis begonias. (1) Size: Considered small to medium; from 6 cm. up to 9 cm. from base to apex. (2) Shape: orbicular, some basal overlap of lobes. (3) Texture: Firm, crisp, but not brittle; glabrous top side, rugose underside. (4) Margin: Serrated. (5) Color: young foliage, top side yellow green 146A with red infusion; underside, from red 53B to yellow green 148AB, with strong red infusion;

mature foliage, top side between green 137A and green 139A, under side yellow green 147C with some red infusion. (6) Venation: Palmate.

Flowering description:

(A) *Flowering habit.*—Is indeterminant, with flowers presented in raceme and supported on strong peduncles. Pedicels are usually close to foliage and continuous, with secondary buds following the primary flowering.

(B) *Natural flowering season.*—Generally flowers in all seasons, being most floriferous in spring and autumn and having slowest flowering in midwinter.

(C) *Flower buds.*—Flat, round, darker than yellow green 145A.

(D) *Flowers borne.*—On short sturdy pedicels originating from strong peduncles resulting in raceme form of terminal flowering first, with additional flowering as raceme develops; flowers are double.

(E) *Quantity.*—Flowering is abundant to highly floriferous depending on environment.

(F) *Tepals.*—(1) Shape: Young tepals tend to have ruffled edges; mature tepals vary in shape. (2) Color: top side in winter when opening yellow 2B, except for outermost two tepals which are yellow green 154BC, tinging to pink on maturity; main color fades to yellow 10BC; under side, first two tepals green 145A; others yellow green 2CD. The flower color of the front lower flowers in the photograph should be disregarded because of reflection due to the set-up of the photograph. (3) Number of tepals: 24–28, often more in spring/fall. (4) Size of tepals: Basal 2.5–3 cm.; others 2 cm. and smaller in center. (5) Flower size: Up to 5–6 cm. in diameter. (6) Open flowers exhibit a darker yellow point in center.

(G) *Reproductive organs.*—Cultivar in sterile triploid.

Disease resistance: More resistant to mildew than most present commercial hiemalis begonia cultivars.

General observations: The outermost two (2) tepals of Romance Too are initially chartreuse yellow in color, and mature to slight pink. The wide open flowers have excellent keeping quality, and their tendency to fade results in considerable individual flower color differences but an overall pleasing color effect.

I claim:

1. A new and distinct cultivar of begonia plant known by the name Romance Too, as described and illustrated, and particularly characterized by its light chartreuse-yellow flower color, which fades to a lighter yellow on maturity, with the outermost petals tinging to pink on maturity; ease of propagation, vigorous growth habit; early flowering, and excellent keeping quality.

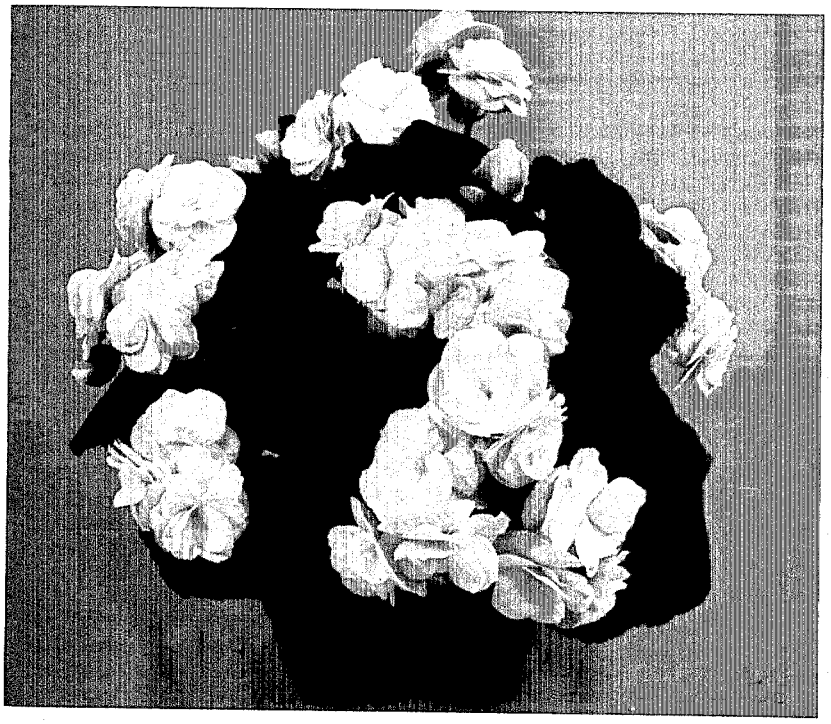

* * * * *